United States Patent [19]

Gui

[11] Patent Number: 5,569,809
[45] Date of Patent: Oct. 29, 1996

[54] METHOD FOR DESTRUCTION OF CHLORINATED HYDROCARBONS

[75] Inventor: John Y. Gui, Colonie, N.Y.

[73] Assignee: General Electric Company, Schenectady, N.Y.

[21] Appl. No.: 497,828

[22] Filed: Jul. 3, 1995

[51] Int. Cl.$^6$ .................................................. C02F 1/461
[52] U.S. Cl. .................... 588/204; 588/212; 205/688; 205/742; 205/779.5; 205/743
[58] Field of Search ............................... 204/149, 153.13, 204/131; 588/204, 212; 205/688, 742, 779.5, 743

[56] References Cited

U.S. PATENT DOCUMENTS

| | | | |
|---|---|---|---|
| 4,343,767 | 8/1982 | Long et al. | 422/70 |
| 4,702,804 | 10/1987 | Mazur et al. | 204/73 R |
| 4,707,230 | 11/1987 | Ajami | 204/131 |
| 4,778,570 | 10/1988 | Van Duin | 204/153.13 |
| 5,107,058 | 4/1992 | Chen et al. | 585/818 |
| 5,391,270 | 2/1995 | Gui et al. | 204/153.1 |

OTHER PUBLICATIONS

"Electrochemical Processing (Inorganic)", vol. 9, pp. 148–158. (no date).
"Electroanalytical Techniques", vol. 9, pp. 88–110. (no date).

Primary Examiner—Arun S. Phasge
Attorney, Agent, or Firm—Noreen C. Johnson; William H. Pittman

[57] ABSTRACT

A method for detecting and destroying various chlorinated hydrocarbons and unsaturated hydrocarbons in the environment using electrochemical techniques has been invented. By concentrating the chlorinated hydrocarbons or unsaturated hydrocarbons in a solvent by liquid-solid or liquid-liquid extraction, and then passing current through the solvent extractant containing the chlorinated hydrocarbons or unsaturated hydrocarbons electrochemically removes chlorine and oxidizes unsaturated hydrocarbons. The potential is measured to correlate to the concentration of the chlorinated hydrocarbon specie.

12 Claims, 8 Drawing Sheets fig. 1 fig. 2

METHOD FOR DESTRUCTION OF CHLORINATED HYDROCARBONS

FIELD OF THE INVENTION

This invention relates to remedial and analytical techniques, and more particularly, to the electrochemical destruction and detection of certain halogenated hydrocarbons in the course of site characterization, process monitoring and control, and remediation of toxic waste materials.

BACKGROUND OF THE INVENTION

The hazards to public health and the environment which are posed by a variety of halogenated organic compounds are well known. Compounds such as polychlorinated biphenyls (PCBs), dichlorodiphenyl trichloroethane (DDT), trichloroethylene (TCE), and chlorinated benzenes have been regulated as environmentally toxic compounds. Due to spills and prior usage, these compounds are often found in soil, sludge and building materials. Their disposal requires a safe and efficient means.

Polychlorinated biphenyls pose a potentially serious environmental problem. Once widely used as dielectric fluid additives in electrical equipment for transformers and capacitors, the use of PCBs has been banned by the U.S. Environmental Protection Agency. Trichloroethylene is ranked as a targeted chemical for clean-up due to its widespread usage as a degreasing solvent. Thus, methods for the removal and destruction of PCBs, trichloroethylene and other chlorinated solvents from contaminated waste sites are sought.

The costs associated with the characterization and remediation of these waste sites are exceedingly high. Various thermal methods for the removal or destruction of halogenated organic compounds, such as incineration, are currently used. Toxic by-products are sometimes produced with this method. An alternative method is soil washing of contaminated materials. The treating chemicals in this method sometimes may pose potential secondary environmental problems. Also, current destructive methods often do not address situations where trace quantities of pollutants are found and need to be destroyed.

There are also problems with the detection of chlorinated hydrocarbons at waste sites. Methods exist for trace analysis of chlorinated hydrocarbons in laboratories, not for rapid and simple detection in the field. These laboratory methods usually require expensive instruments, well-controlled operation conditions, and lengthy sample preparations. These analysis procedures are time consuming and expensive.

Thus, a need exists for a method to remediate contaminated materials which do not require excessive amounts of various reagents, do not produce toxic by-products, is relatively inexpensive, and obtains acceptable removal and destruction levels of contaminants.

SUMMARY OF THE INVENTION

The invention satisfies this need by detecting and destroying various chlorinated hydrocarbons and unsaturated hydrocarbons in the environment using electrochemical techniques. The method to destruct chlorinated hydrocarbons and unsaturated hydrocarbons found in gaseous media, aqueous solutions, and solid materials comprises the steps of concentrating the chlorinated hydrocarbons or unsaturated hydrocarbons in a solvent by liquid-gas, liquid-solid, or liquid-liquid extraction, and then passing current under a controlled potential through a solvent extractant containing the chlorinated hydrocarbons or unsaturated hydrocarbons for a period of time sufficient to electrochemically remove chlorine from chlorinated hydrocarbons or oxidize unsaturated hydrocarbons, in an electrolysis cell with a working electrode which can be reactivated through electrochemical oxidation and reduction. Electrochemical reduction is effective for destroying chlorinated hydrocarbons because of the relatively easy removal of chlorine atoms from the parent compound as chloride ions (Cl–).

A preconcentration of the organic pollutants, herein meaning chlorinated hydrocarbons and unsaturated hydrocarbons, in a liquid solvent involves step-by-step or continuous in-situ liquid-gas, liquid-liquid, or liquid-solid extraction from the contaminated material. This preconcentration is necessary for detecting, and especially for destroying trace amounts of organic pollutants because of severe interference from various environmental substrates, limited resolution and sensitivity of electrochemical techniques, and restricted applicable potential range in which pollutants can be electrochemically destroyed.

Chlorinated hydrocarbons can include perchloroethene (PCE), trichloroethene (TCE), dichloroethenes (DCE), vinyl chloride, tetrachloroethane, 1,1,1-trichloroethane, carbon tetrachloride, chloroform, polychlorinated biphenyls, and mixtures thereof. Other halogenated hydrocarbons, chlorinated, brominated, and iodinated, may also be treated by the method of this invention.

Another important aspect of this invention is an in-situ electrochemical activation of the electrode surface used in the electrochemical destruction process. In conventional electrochemical reactions, the electrode surface generally becomes deactivated after a short time of electrolysis. In this invention the electrode surface is kept active during the destruction of the pollutants.

In addition to destroying chlorinated organic pollutants, this invention also provides a method for detecting and measuring the chlorinated organic pollutants, such as polychlorinated biphenyls (PCBs), trichloroethene (TCE), and carbon tetrachloride in gas, liquid, and solid media. The method is based on the effective extraction and preconcentration of chlorinated hydrocarbons from various environmental substrates into an organic solvent, followed by the electrochemical analysis of the targeting chlorinated hydrocarbons based on the electro-reductive dechlorination. Therefore, the method for detecting and quantifying chlorinated hydrocarbons includes extracting the chlorinated hydrocarbons from gas, aqueous, or solid media into an organic solution, electrochemically applying a negative potential to a working electrode to dechlorinate the chlorinated hydrocarbons in the organic solvent, and measuring a current or charge generated to determine the chlorinated hydrocarbon concentration.

The described electroanalytical method is fast and simple which uses a portable instrument that can be taken to field sites. The combination of extraction-preconcentration of the organic pollutants to detect, measure, and destroy the hydrocarbons provides significant economical savings for environmental site characterization and remediation process monitoring for polychlorinated biphenyls, trichloroethylene, and other hazardous chlorinated hydrocarbons.

BRIEF DESCRIPTION OF THE DRAWINGS

FIGS. 8 A–B show cyclic voltammograms of dimethylformamide solution containing 5 mM carbon tetrachloride at the glassy-carbon electrode (A) and platinum electrode (B). Platinum serves as the auxiliary electrode and Ag/AgCl as the reference electrode. Scan rate 100 mV/s; electrolyte 0.01M TEAP.

FIGS. 9 A–C show cyclic voltammograms of dimethylformamide solution containing 171 ppm Aroclor 1242 at the glassy-carbon electrode by linear scan (left), square wave (center), and differential pulse (right) techniques. Platinum serves as the auxiliary electrode and Ag/AgCl as the reference electrode.

STATEMENT OF THE INVENTION

Chlorine atoms on most chlorinated hydrocarbons can be electrochemically stripped from the parent compounds. As a result, this electrochemical process can be used as a destruction and detection method for chlorinated hydrocarbon pollutants.

The electrochemical dechlorination is achieved by applying a negative potential to a working electrode immersed in an electrolyte solution containing chlorinated hydrocarbon pollutants. The electrochemical cell may contain a few milliliters to liters of organic solvent and three electrodes. An organic salt should also be added into the solvent to provide sufficient electric conductivity. A piece of metal, such as Platinum wire, can serve as an auxiliary electrode. A reference electrode, such as silver/silver chloride, is employed for accurate control and measurement of working electrode potential. The working electrode provides a surface where the targeted chlorinated hydrocarbons can be reduced readily in the potential range where the solvent will not interfere. A glassy-carbon electrode is the preferred electrode for chlorinated hydrocarbon reduction.

Most chlorinated hydrocarbons are non-ionic compounds and thus, can easily be extracted from other substrates into an organic solvent because they, by their chemical and physical nature, prefer to be dissolved in the organic phase rather than in aqueous and soil phases. Although both polar and non-polar organic solvents can be used for extraction, the polar organic solvents are preferred for extraction because only polar organic solvents can be used as an electrolyte solution for electroanalysis and electrodestruction.

Typical electrolyte solutions contain small amounts of organic salts in polar organic solvents such as acetonitrile, N,N'-dimethylformamide (DMF), propylene carbonate (PC), and dimethyl sulfoxide (DMS). Since the chlorinated hydrocarbon pollutants are normally present in gas, soil, or aqueous media, transferring them into an organic electrolyte solution has to be achieved.

For rapid analysis of chlorinated hydrocarbons in relatively dry solid substrates, direct extraction with a polar organic solvent, such as acetonitrile, can be used. The extract is filtered and the filtrate is analyzed electrochemically without further separation. For an aqueous or a wet soil environmental sample, a non-polar organic solvent can be used for extraction because polar solvents are miscible with water. Pollutants extracted into nonpolar solvents need to be mixed with a polar organic electrolyte before electroanalysis.

For in-situ detection of chlorinated hydrocarbons in aqueous streams, an indirect extraction of chlorinated hydrocarbons from the aqueous phase to the organic phase can be accomplished by using a polymer membrane cell. The chlorinated hydrocarbons in the aqueous phase, driven by their partition equilibriums, absorb into the membrane, then diffuse into the organic solution where they can be electrochemically analyzed. The polymeric membrane can be natural or synthesized materials such as rubber and Teflon, in various forms such as thin-wall tubing and sheet. This membrane extraction-electroanalysis methodology is particularly useful for detecting chlorinated hydrocarbons in surfactant solutions employed in soil washing because direct extraction may result in the formation of suspension or emulsion, which is unapplicable for electroanalysis.

The pollutants in an aqueous sample are forced into contact with an organic solid phase which strongly absorb/adsorb the organic pollutants, or effectively transport the pollutants but not the water. The solid phase can be either a thin-layer polymer film, gel or membrane. Such a solid phase acts as both a preconcentrator because the chlorinated hydrocarbons prefer to be in the organic phase than the aqueous phase and a separator because only uncharged pollutants will be collected into the solid phase and water and charged species are left behind. The pollutants dissolved into the solid phase can then be extracted out into an organic solvent and be destructed by electrochemistry. Organic solvents are polar, water miscible solvents. Examples are dimethylformamide, acetonitrile, propylene carbonate, and mixtures thereof.

To ensure the complete destruction, the working electrode should be placed as close to the solid phase. For instance, one can coat electrode material such as carbon onto the surface (in contact with an organic electrolyte) of solid phase such as porous Teflon tubing as the working electrode.

Now referring to the electrochemical cell, the useful potential range depends mainly on the electrochemical nature of the electrolyte solution, the working electrode surface, type of pollutants and the matrix interfering species. The temperature and pressure also influence the selection of the potential that is applied to the electrode. In general, the destruction potential should be set to a value where pollutants can be dechlorinated, but the electrolyte solution and the electrode surface remain unaffected. Thus, the selection of the electrolyte and electrode is very important for a specific application.

Typical electrodes are metals such as platinum, gold, silver, palladium, iron, nickel, glassy carbon, graphite, various forms of carbon fibers and clothes, alloys such as stainless steel, carbon steel, and some specialty electrodes, such as metal oxides and chemically modified electrodes.

A problem encountered with continuous electrolysis is the working electrode deactivation. In this invention, a deactivated electrode surface as the result of prolonged reduction can be reactivated by applying a positive potential to oxidize the residuals that are deposited onto the electrode surface and regenerate surface electrochemical active sites.

For electrochemical destruction, a fixed potential or current is generally applied. In a fixed potential mode, a constant or a series of reduction or oxidation potential is applied to a working electrode where pollutants are reductively destroyed. By choosing a proper potential, one can selectively destruct a particular pollutant. The destruction current usually decreases with the electrolysis time because the pollutant concentration decreases as the electrolysis proceeds. In a fixed current mode, a constant or a series of anodic or cathodic current is applied to the electrode. The potential at the electrode varies during the electrolysis. For example, the potential shifts to more negative potential during an electrolysis at a fixed cathodic current.

For electrochemical detection, a cathodic potential scan, scanning to more negative potentials, is used. There are several potential scanning waveforms. The commonly used waveforms are differential pulse (DP), square wave (SW), and linear scan (LS) voltammetry. Tests have indicated that while the linear scan is fastest, it is the least sensitive. The differential pulse is highly sensitive but the slowest method. The square wave potential scan is the best choice with the differential pulse sensitivity and the linear scan speed.

In the detection method of this invention, depending on their chemical structure, different chlorinated hydrocarbons or different chlorine atoms on the same chlorinated hydrocarbon will be dechlorinated at different reduction potentials. The reduction potential reveals possible chlorinated hydrocarbon identity. The current or charge generated during the reduction process is proportional to the chlorinated hydrocarbon concentration. Thus, it can be used to quantitate the chlorinated hydrocarbon concentration while also indicating the extent of the destruction process. A relationship exists between the amount of chlorinated hydrocarbons in the sample and the stripping current. The amount ("C") of chlorine can be calculated according to the equation $$C=KY+b$$

wherein C is the concentration (ppm) of the particular chlorinated hydrocarbon in the solution prepared for the sample; Y is the peak current (uA) and charge (uC) value determined by way of a voltammogram; K is the precalculated slope for a calibration curve C plotted against Y (C vs. Y); and b is a constant.

The following examples further serve to demonstrate the invention.

EXAMPLE 1

ELECTROCHEMISTRY OF CHLORINATEED ETHENES

Figure 1:
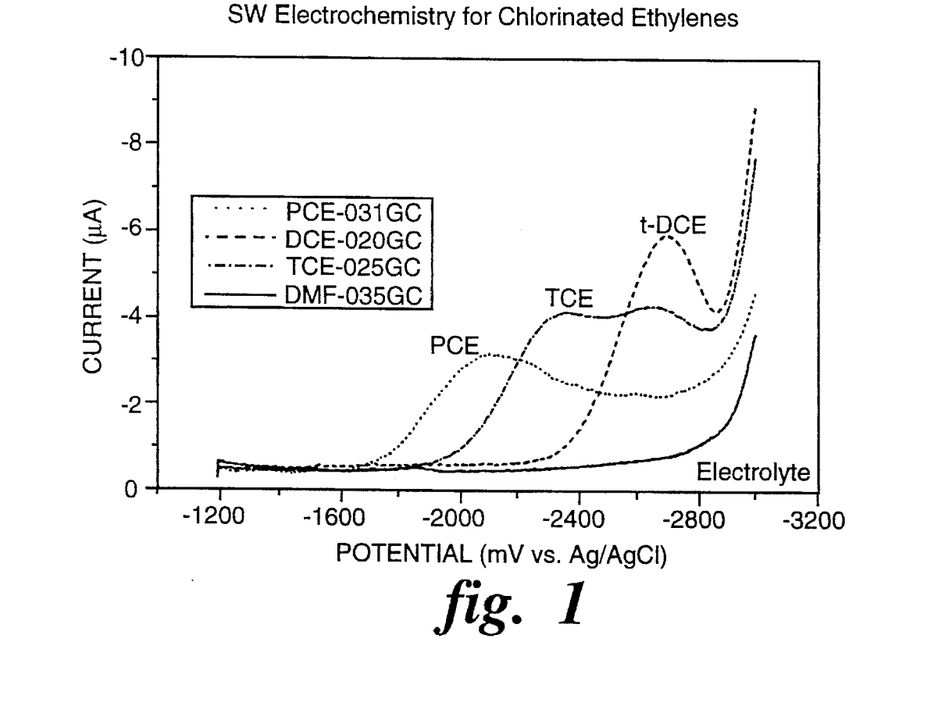
FIG. 1 shows the square-wave voltammograms of dimethylformamide (DMF) solution containing 10 mM chloroethenes at the glassy-carbon electrode. Platinum serves as the auxiliary electrode and Ag/AgCl as the reference electrode. Square wave parameters: amplitude, 30 mV; potential step, 2 mV; period, 100 ms. Electrolyte: 0.02 TEAP (tetraethylammonium perchlorinate).
Figure 2:
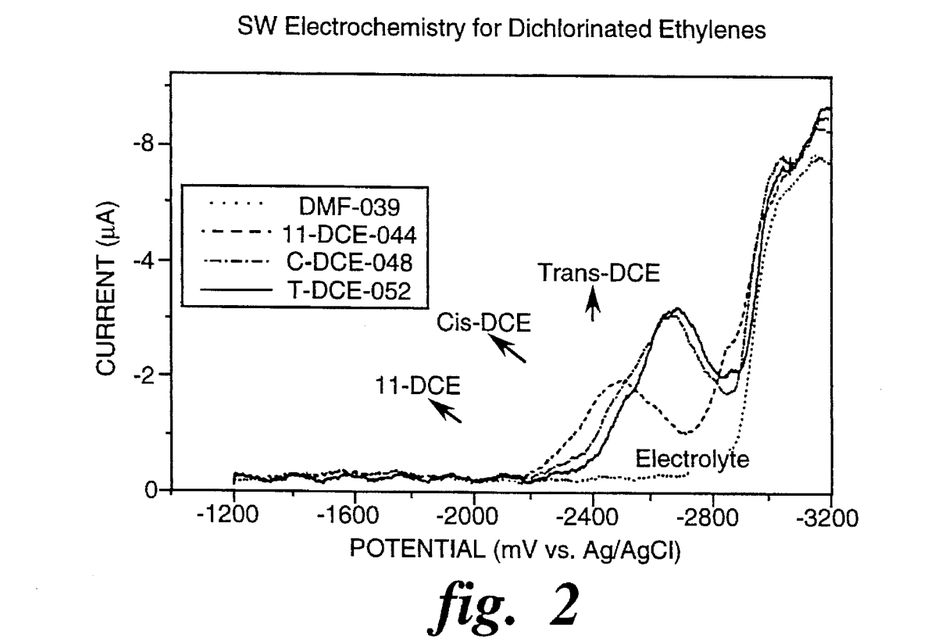
FIG. 2 shows the square-wave voltammograms of dimethylformamide solution containing 10 mM chloroethenes at the glass-carbon electrode. The electrochemistry for dichlorinated ethylenes is shown. Other experimental conditions as in FIG. 1.

Chlorinated ethenes can be electrochemical dechlorinated stepwise to ethene. Ethene under extremely negative potentials can be further reduced to ethane through the hydrogenation at proper conditions. Presented in FIG. 1 are the square-wave (SW) voltammograms of tetrachloroethene (perchloroethene, PCE), trichloroethene (TCE) and trans-dichloroethene (t-DCE). For comparison purpose, the SW voltammogram of the electrolyte is also given. The figure clearly shows the readiness for dechlorination is in the order of PCE>TCE>t-DCE. The results also revealed the stepwise dechlorination mechanism at the electrode surface as illustrated by the continuous reduction peaks (shoulders) following the first major reduction peak for PCE and TEC. The peaks' potentials indicate the possible intermediates. For example, the first reduction intermediate for PCE is likely to be TCE, which can be further reduced to DCE(s). Since there are three possible DCE isomers, 1,1-DCE, cis-DCE and trans-DCE, the first reduction intermediate(s) for TCE can be one or two or all of them depending which chlorine atom is going to be removed. To investigate this, electrochemical reduction experiments were carried out; for all three DCEs and the results are displayed in FIG. 2. The voltametric results indicate that 1,1-DCE is more readily reducible than other two because it has the most positive reduction potential. This is expected because two chlorine atoms in 1,1-DCE are attached to the same carbon which is considered less stable than attached to different carbons as in the case of cis-DEC and trans-DCE. By comparing the SW voltammograms of TCE in FIG. 1 and those of DCEs in FIG. 2, it is shown that 1,1,-DCE is unlikely to be the intermediate for TCE reduction because of the potential mismatch. Identification of whether cis-DEC or trans-DCE is the only TCE reduction intermediate is impossible due to the lack of substantial potential differentiation.

EXAMPLE 2

ELECTRODE EFFECT ON ELECTROCHEMICAL REDUCTION OF CHLOROETHENES

Figure 3A:
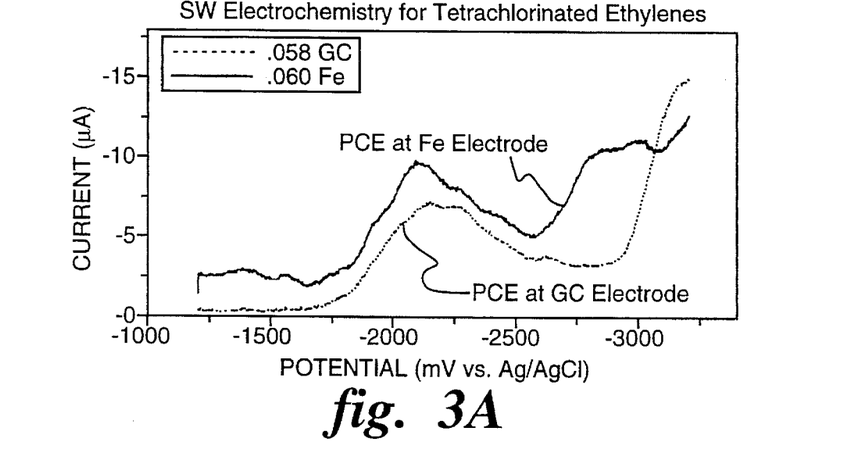
FIG. 3 compares the square-wave voltammograms of 10 mM chloroethenes, [PCE (A), TCE (B), and trans-DCE (C)] at the iron (solid curves) and glassy-carbon (dotted curves) electrodes in dimethylformamide. The working electrodes are 1 mm diameter disks. Platinum serves as the auxiliary electrode and Ag/AgCl as the reference electrode. Other experimental conditions as in FIG. 1.
Figure 3B:
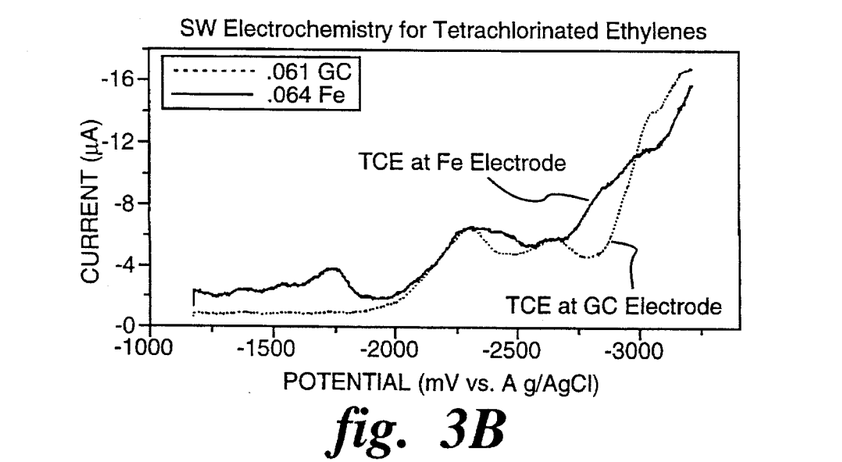
Figure 3C:
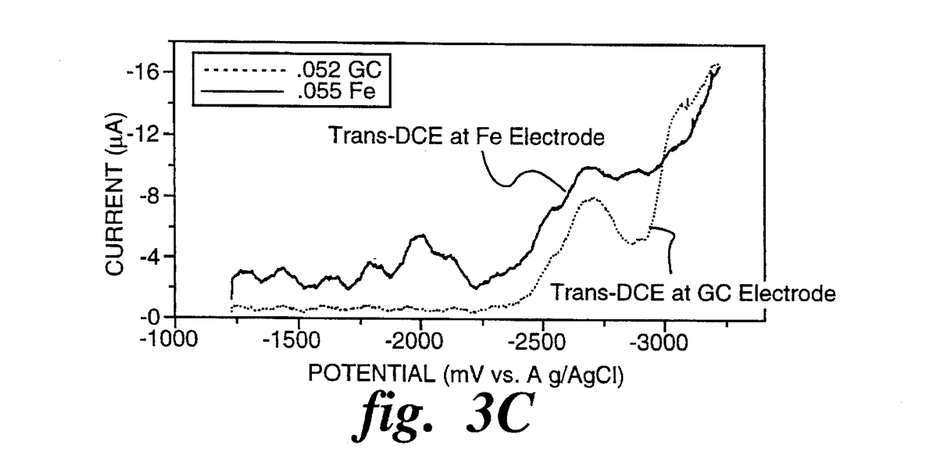

Electrode material has great effect on the electrochemical behavior of chlorinated hydrocarbon (CHC) compounds. Shown in FIG. 3 are the SW voltammograms of PCE, TCE and trans-DCE in dimethylformamide (DMF) at the iron and glassy-carbon electrodes. There is one similarity and two differences between two electrodes for all three chloroethenes. The similarity is that the first bulk reduction peaks (−2.13 V for PCE, −2.31 for TCE and −2.67 V for t-DCE) are essentially the same. The first difference is that there are several reduction pre-peaks before the bulk reduction peaks at the iron electrode, but no pre-peak can be observed at glassy-carbon electrode. The complexity of pre-peaks increases with the decrease of chlorination of ethene. The other difference is that there is a broad post-peak reduction band between −2750 to −3000 mV at the iron electrode, which is not observed on the glassy-carbon electrode. This band current decreases with the decrease of chlorination of ethene.

These pre-peaks and post bands are most likely to be contributed by the surface adsorbed species. Chloroethenes may chemically adsorbed onto iron surface in different forms which may be reductively desorbed at different electrode potentials more positive than the bulk reduction potential. Adsorbed chloroethene species can also be more difficult to be reduced than the bulk species, thus they will be reduced at more negative potential than the bulk species. Unlike the iron surface, the glassy-carbon surface is much inert in term of chemical adsorption. Thus only bulk reductions are observed. From the above example, one can conclude that glassy-carbon electrode is the choice for analytical purpose because it produces better defined reduction peaks and the peak height is proportional to the bulk analyte concentration, while Fe electrode may be better for the destruction of chloroethenes because surface species can facilitate the reductive dechlorination process.

EXAMPLE 3

ELECTROCHEMICAL DESTRUCTION CHLORINATED HYDROCARBONS

Most chlorinated hydrocarbons can be destroyed either through electrochemical reduction or oxidation. Depending on whether the hydrocarbon structure is saturated or not, there may be two different reduction processes. The first one is the dechlorination in which chlorine atom(s) is reductively stripped off through the reduction as chloride ion. The second one is the hydrogenation process in which the unsaturated hydrocarbon(s) is hydrogenated through the addition of hydrogen atoms. The electrochemical oxidation of hydrocarbons can proceed through multiple stages and final oxidation products can be carbon dioxide and water. For destroying chlorinated hydrocarbons, the electrochemical reduction is more feasible than the oxidation because of the electronegativity of chlorine.

Figure 4:
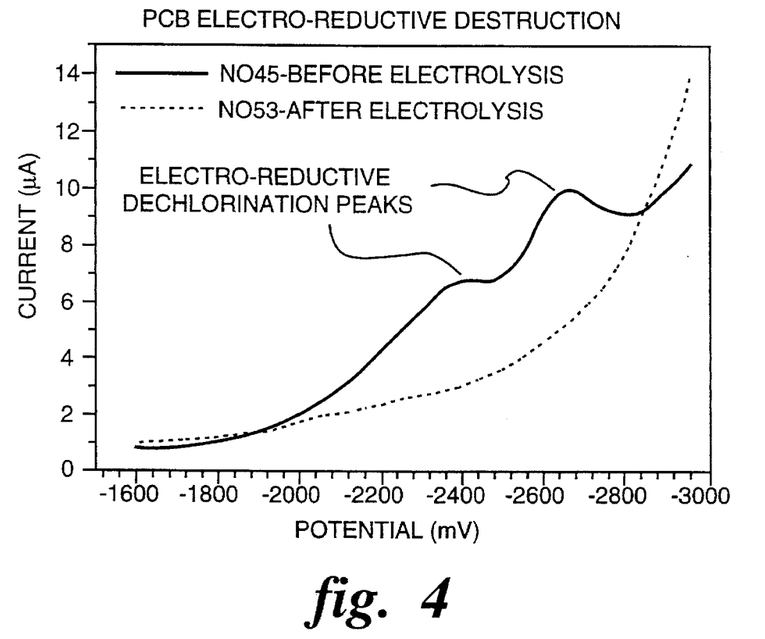
FIG. 4 shows linear sweep voltammograms at glassy-carbon electrode before (solid curve) and after (dotted curve) the electrolysis of 171 parts per million Aroclor 1242 in dimethylformamide. Platinum serves as the auxiliary electrode and Ag/AgCl as the reference electrode.

Displayed in FIG. 4 are the linear sweep voltammograms taken just before and after the reductive electrolysis of 171 ppm Aroclor 1242 in DMF. Clearly, most of PCBs are disappeared after two hours reduction in a stirred electrolysis cell at −3.0 V as judged from the deceased PCB reduction peaks around −2.36 V and −2.64 V. The reductive dechlorination has also been confirmed by the liquid chromatogram analysis.

Figure 5:
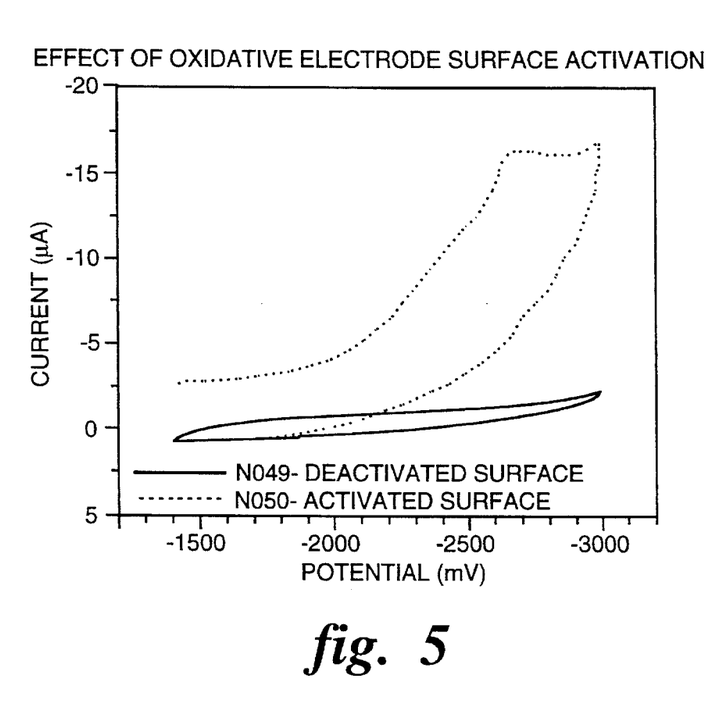
FIG. 5 shows cyclic voltammogram of a deactivated (solid curve) and the reactivated glassy-carbon electrode (dotted curve) in dimethylformamide containing partially electrolyzed Aroclor 1242. Platinum serves as the auxiliary electrode and Ag/AgCl as the reference electrode.

Electrode surface deactivation due to surface contamination or polymerization is a common problem for organic electrolysis. However, it can be overcome through either mechanical electrode cleaning or in-situ electrochemical cleaning. Mechanic cleaning can be done either by taking the electrode out to resurface it or be cleaning the electrode in the cell through a polishing device. Electrochemical cleaning is achieved through the either extreme oxidation or reduction depending on the nature of surface deactivation. Sometimes the combination of both oxidation and reduction is more beneficial. Ultrasonification have also been found to be effective to enhance the electrochemical cleaning. Compared in FIG. 5 are cyclic voltammograms of a deactivated (solid curve). and the reactivated glassy-carbon electrode (dotted curve) in DMF containing Aroclor 1242 which had undergone some degree of electroreduction at −3.0 V. The electrode reactivation was accomplished by applying 1.46 V to the deactivated GC electrode for a few minutes. The oxidation potential and time are important to achieve clean, but reproducible active electrodes. Periodical potential stepping between cleaning oxidation and reduction is also effective. The advantages of electrochemical cleaning over the mechanical cleaning are simpler, faster, and reproducible.

EXAMPLE 4

INVESTIGATION OF ELECTROCHEMICAL PROPERTIES OF CHLORINATED HYDROCARBONS POLLUTANTS

Figure 6:
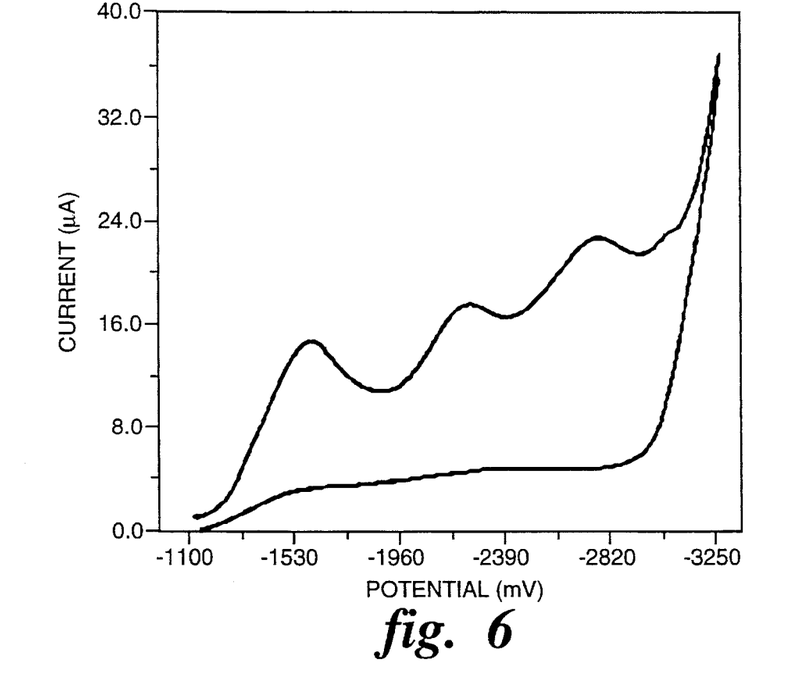
FIG. 6 shows a cyclic voltammogram of dimethylformamide solution containing 5 mM carbon tetrachloride at the glassy-carbon electrode. Platinum serves as the auxiliary electrode and Ag/AgCl as the reference electrode. 0.01M TEAP was used as electrolyte. Scan rate 100 mV/s.
Figure 7:
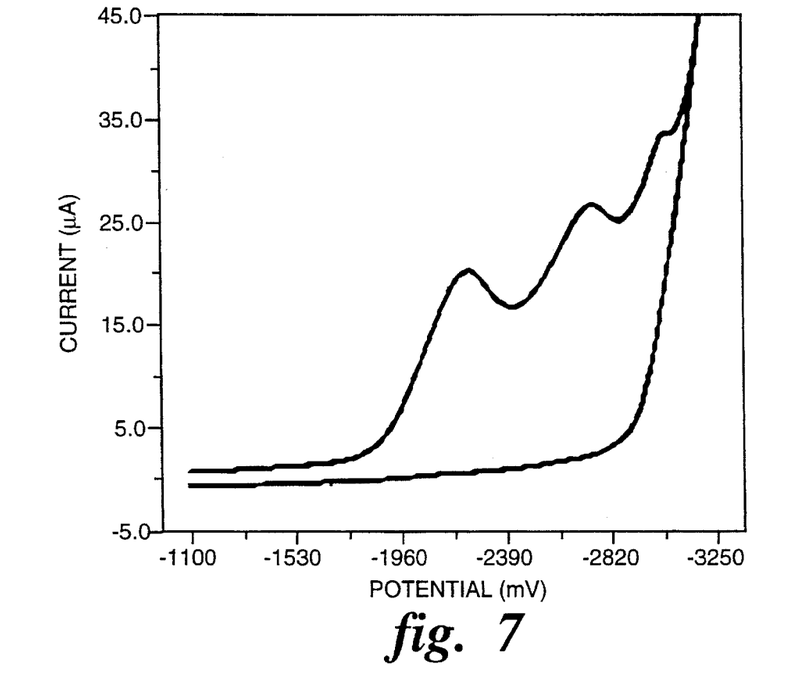
FIG. 7 shows a cyclic voltammogram of dimethylformamide solution containing 4.18 mM $CHCl_3$ at the glassy-carbon electrode. Platinum serves as the auxiliary electrode and Ag/AgCl as the reference electrode. Scan rate 200 mV/s; electrolyte 0.01M TEAP.

In pursuing the feasibility for chlorinated hydrocarbon electroanalysis, studies have been carried out to investigate their electrochemical properties in organic solvents such as DMF (dimethylformamide). By applying sufficient negative potential to a working electrode, a chlorinated molecule can undergo a stepwise reduction by stripping off its chlorine atoms. For example, carbon tetrachloride ($CCl_4$) can be electrochemically reduced according to the following mechanism as revealed by the four cathodic peaks shown in FIG. 6:

The cyclic voltammogram was obtained for 5 mM $CCl_4$ in DMF with TEAP (tetraethylammonium perchlorinate) as the supporting electrolyte at the glassy carbon electrode. The above mechanism is further supported by the results displayed in FIG. 7 for the electrochemical reduction of chloroform, which yields the same three cathodic peaks as the last three peaks for $CCl_4$.

Unsaturated chlorinated hydrocarbons can be electrochemically reduced by dechlorination and hydrogenation. But dechlorination usually occurs at potentials much more positive than those for hydrogenation, as can be seen from later examples. These electrochemical properties thus allow the detection of unsaturated chlorinated hydrocarbons in the presence of nonchlorinated unsaturated compounds.

Figure 8A:
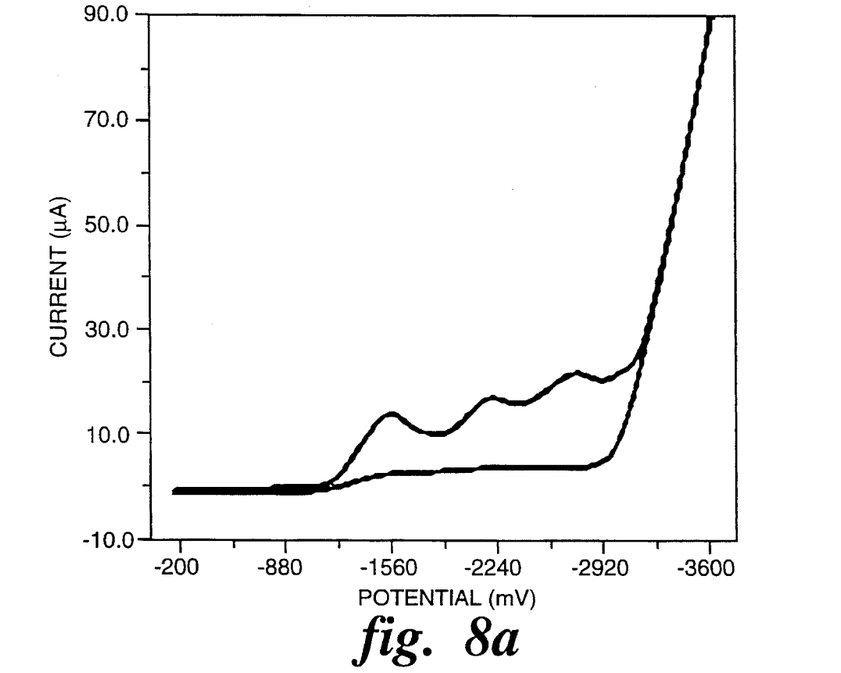
Figure 8B:
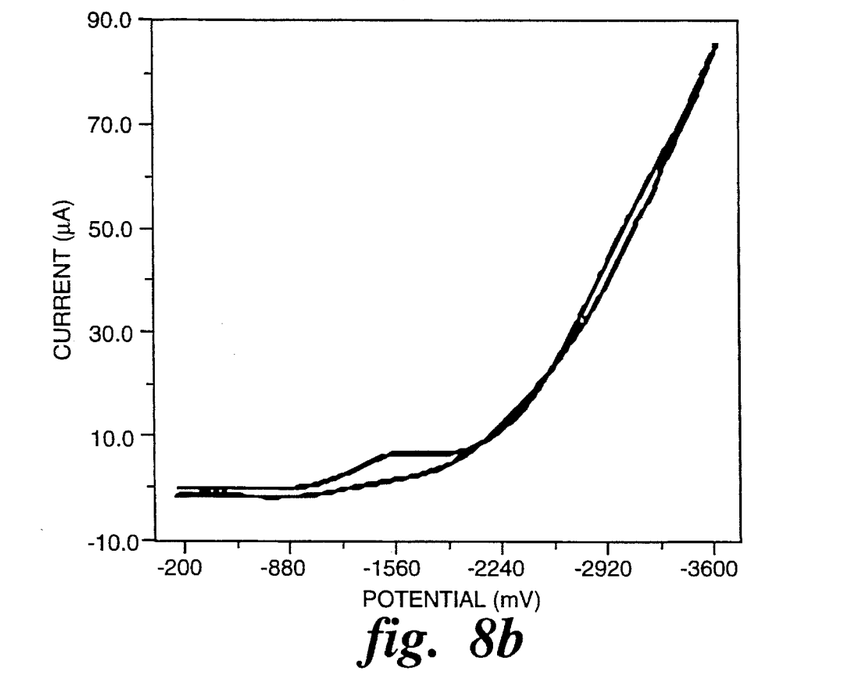

Electrode material has great effect on the electrochemical behavior of chlorinated hydrocarbon compounds. Shown in FIG. 8 are the voltammograms of 5 mM $CCl_4$ in DMF at the platinum (A) and glassy carbon (B) electrodes.

The glassy carbon electrode yields much better defined reduction peaks than the platinum electrode. The similar phenomenon was also observed for the reductive dechlorination of Aroclors in DMF. Platinum electrode gives a broad reduction band without any distinguishable peak, while glassy carbon electrode produces distinct reduction peaks. Glassy carbon electrode is a preferred choice for analytical purpose.

Figure 9A:
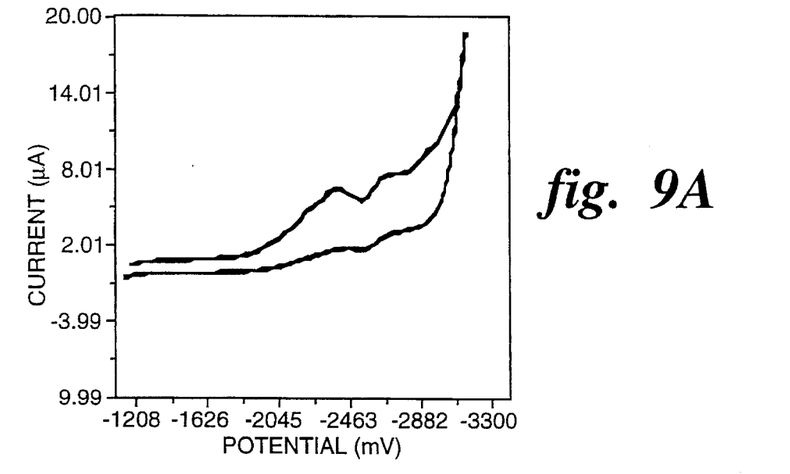
Figure 9B:
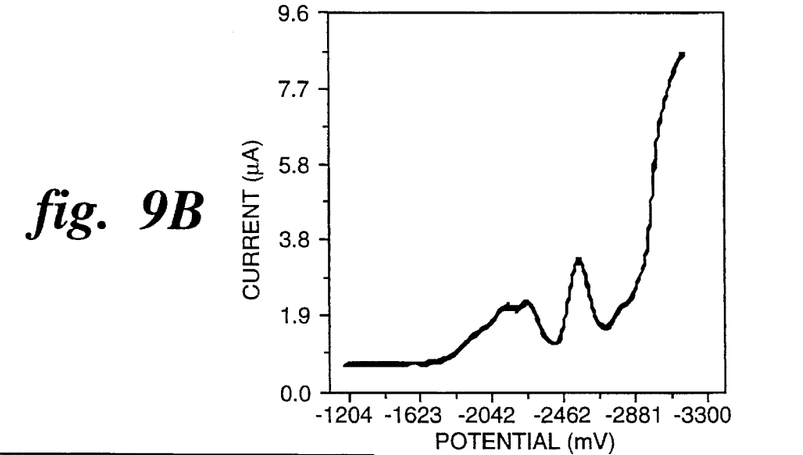
Figure 9C:
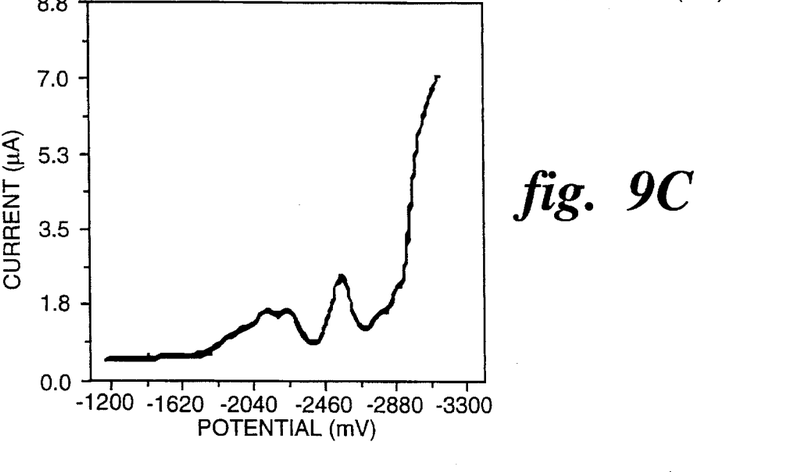

Electroanalytical results were also dependent on the potential scan waveform. Shown in FIG. 9 are the voltammograms obtained by three potential waveforms: LS (linear scan), SW (square wave) and DP (differential pulse). The SW and DP voltammetric methods produce better defined reduction peaks than the LS method. SW is much faster than DP in data acquisition.

EXAMPLE 5

SIMPLE AND RAPID ANALYSIS FOR PCBS IN SOIL

Figure 10:
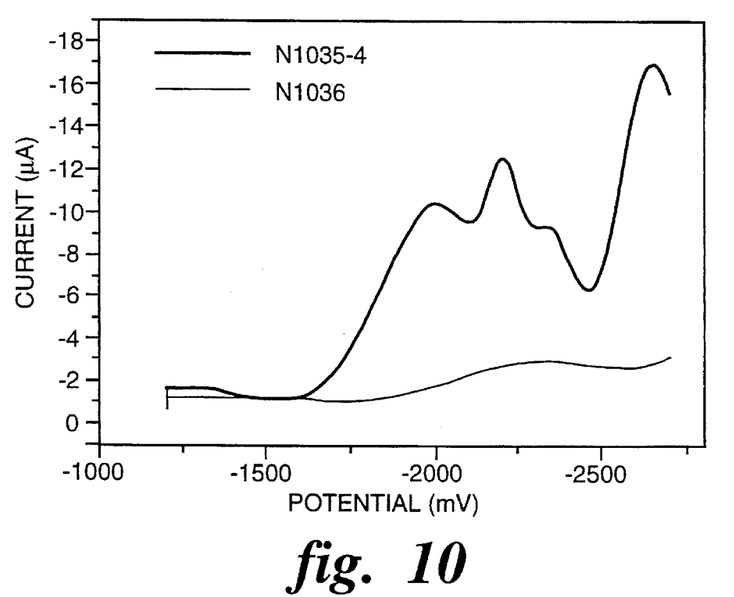
FIG. 10 shows square wave voltammograms of dimethylformamide solutions extracted from the EPA-SSM clean soil (lower curve) and the same soil doped with 1000 ppm Aroclor 1254 (upper curve). The extraction time is ten minutes. Glassy-carbon is the working electrode. Platinum serves as the auxiliary electrode and Ag/AgCl as the reference electrode.

Shown in FIG. 10 are the experimental results obtained for two soil samples by DMF extraction and square-wave electroanalysis. Both soil samples are based on an EPA standard soil mixture (SSM) except one is doped with 1000 ppm Aroclor 1254 and the other is not. The experiment was carried out by the following simple procedures:

1. Weigh 5.0 g of soil into a vial containing 5 ml of DMF electrolyte and 4 stainless-steel balls.
2. Shake the vial for 10 minutes.
3. Filter the extract solution with a plunge-barrel type filter.
4. Run SW voltammetry in the filtrate.

From the voltammograms displayed in FIG. 10, one can observe the following:

The Aroclor doped into the soil is 1254 because the voltammographic signature matches that of the pure Aroclor 1254 in DMF as obtained earlier. The first three reduction peaks are most likely the results of dechlorination of three types of chlorines in the o-, m- and p- positions and the last peak is probably due to the hydrogenation of the biphenyl ring. The soil has small amounts of reducible organic components in it because the clean soil yields a small and broad reduction background current around −2250 mV. However, there is very little aromatic organics in the soil because the voltammogram of the clean soil yields no observable reduction peak around −2700 mV.

The above example clearly illustrated the usefulness and the advantages of this simple, portable and rapid electroanalytical method for analyzing PCBs in soil.

EXAMPLE 6

RAPID ELECTROANALYSIS OF PCB AND OIL IN SURFACTANT SOLUTION

It has been a big problem for rapid analysis of PCBs in the presence of transformer oils in surfactant solution by spectroscopic methods. Electroanalytical technique has possessed the capability to distinguish them. However, rapid removal of PCB from surfactant solution to the organic solution is a challenge. In this experiment small disposable filters stuffed with LOMOD powders were used to extract PCBs out of surfactant solution into the LOMOD which is one of the most effective polymers for removing PCBs in aqueous solutions. The loaded PCBs were then flushed out with the DMF solvent.

The detailed experimental procedures can be described as follows:

1) Passing 10 ml surfactant solution through a prepackaged LOMOD column using a 10 ml syringe.
2) Wash the column with 2 ml DMF containing 0.02M TEAP as electrolyte and collect the effluent into a 2 ml electrochemical cell.
3) Connect the electrodes and run the electroanalysis.

Figure 11:
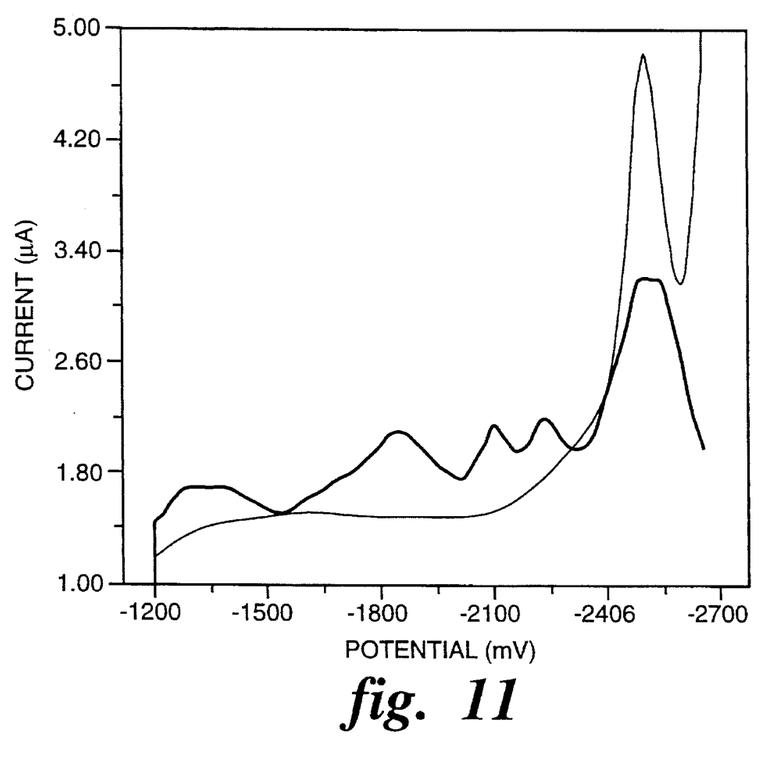
FIG. 11 shows square wave voltammograms of dimethylformamide solution containing 112 ppm Aroclor 1254 and 1100 ppm 10 C Oil (upper curve) and that containing 10 C Oil only (lower curve) at the glassy-carbon electrode. Platinum serves as the auxiliary electrode and Ag/AgCl as the reference electrode.

Displayed in FIG. 11 are the square-wave voltammograms of DMF extracting solutions from two soil washing surfactant solutions: one contains 112 ppm Aroclor 1254 and 1010 ppm 10 C oil, and the other contains 1100 ppm 10 C oil only. As can be seen from the figure, there are three distinct reduction peaks for Aroclor 1254 in the potential range from −1.6 to −2.3 V (vs. Ag/AgCl). There is no electroreduction activity for 10 C oil in this potential range. The above results have clearly revealed the following advantages for electroanalysis:

1. The presence of 10 C oil doesn't interfere with the PCB analysis.
2. Ability to identify different Aroclors.
3. Fast analysis time, typically 10 minutes per sample.
4. Easy modification to an on-line monitoring system for the soil washing.

When the analysis speed is not important, another simple and convenient way to detect ppm or ppb level of Aroclors in an aqueous solution by electrochemistry is the one-step extraction/preconcentration approach. For example, by immersing a thin-wall polymer container such as polyethylene bulb containing small amount (2 ml) of organic solvent (e.g. dimethylformamide) into a PCB-containing aqueous solution (200 ml, 1% surfactant), 100 fold increase in PCB concentration can be achieved.

After stirring the surfactant solution overnight, the DMF solution was taken out and analyzed by SWV (square wave voltammetry). The results showed that the DMF extract from the 1% Tween 20 solution containing no PCB shows no reduction peaks, while the extracts from 0. 112 ppm and 46.1 ppm Aroclor 1254 solutions exhibited the reduction peaks proportional to their concentration. This extraction/preconcentration approach is very useful for sampling and on-site analysis of pollutants in aqueous environments.

EXAMPLE 7

IN-SITU PCB MONITORING FOR SOIL WASHING PROCESS

This example demonstrates the feasibility of electroanalysis for rapid and on-line monitoring of PCBs in soil washing process by the application of a membrane-based electrochemical cell. The membrane should be highly impermeable to water.

Figure 12:
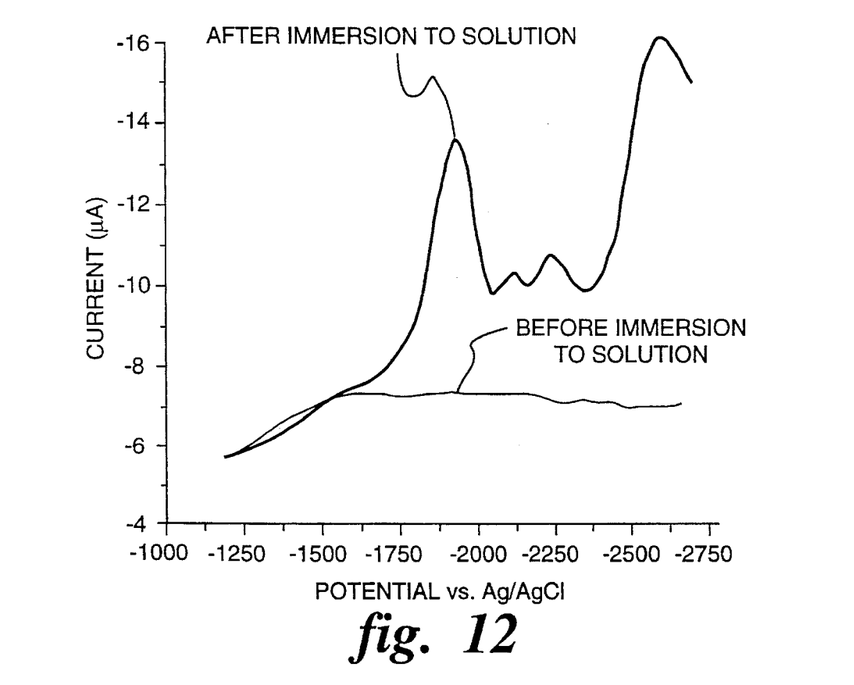
FIG. 12 shows square wave voltammograms of dimethylformamide solution in the latex-cell before (dotted curve) and after (solid curve) contact with the surfactant solution containing 112 ppm Aroclor 1254 and 1010 ppm 10 C Oil at the glassy-carbon electrode. Platinum serves as the auxiliary electrode and Ag/AgCl as the reference electrode.

The membrane separates the aqueous solution from the DMF electrolyte. Organic components such as oil and PCBs are sorbed into the membrane, then dissolved into DMF solution where they are analyzed electrochemically. Due to the large ratio of aqueous solution to DMF solution, PCB preconcentration can be easily achieved by increase of contact time between the membrane-cell with the soil washing solution. The method sensitivity increases with the increase of contact time. Shown in FIG. 12 is the typical result obtained using this membrane-cell. The dotted and solid lines were obtained before and after the membrane-cell was immersed into the surfactant solution, separately. The result clearly demonstrates the feasibility of this in-situ, real-time PCB rapid analytical technique. By making working or all electrode(s) onto the polymer membrane, one should be able to significantly improve the method's response time and sensitivity.

EXAMPLE 8

IN-SITU ELECTROANALYSIS OF VOLATILE CHLORINATED ORGANICS

Figure 13:
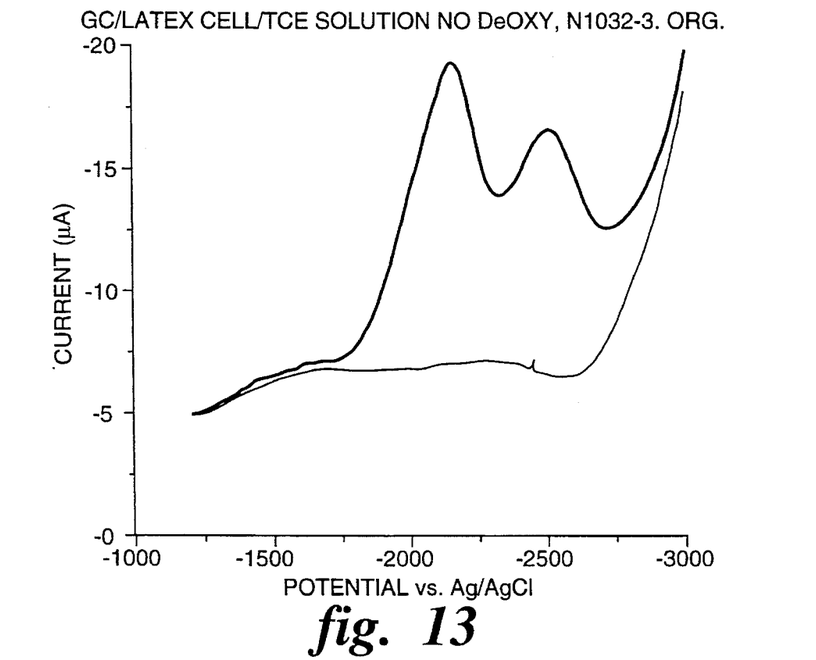
FIG. 13 shows square wave voltammograms of dimethylformamide solution in the latex-cell before (dotted curve) and after (solid curve) exposed to trichloroethylene vapor at the glassy-carbon electrode. Platinum serves as the auxiliary electrode and Ag/AgCl as the reference electrode.

Similar to the electroanalysis of PCBs, the method described above can also be applied to detect volatile chlorinated organics. For example, a membrane-cell was placed into a closed vial containing 5 ml TCE-saturated aqueous solution. The volatile organic molecules in the solution evaporate and diffuse into the DMF solution through the membrane. They are then detected by square-wave voltammetry. After less than 4 minute contact with the TCE vapor in the closed vial, the voltammogram displayed two large reduction peaks (see FIG. 13) characteristic to TCE electroreduction at the GC electrode.

What is claimed is:

1. A method to destruct electrochemically chlorinated hydrocarbons pollutants or unsaturated hydrocarbons found in gaseous media, aqueous solutions, and solid material in an electrochemical cell comprising the steps of: concentrating the chlorinated hydrocarbons or unsaturated hydrocarbons in a solvent by liquid-gas, liquid-solid, or liquid-liquid extraction, and then passing current in the electrochemical cell at a controlled potential through a solvent extractant containing the chlorinated hydrocarbons or unsaturated hydrocarbons for a period of time to electrochemically remove chlorine from the chlorinated hydrocarbons or hydrogenate the unsaturated hydrocarbons at a working electrode, where said electrolysis cell contains three electrodes consisting of a working electrode, an auxiliary electrode, and a reference electrode, and where said working electrode is in-situ reactivated for reuse through electrochemical oxidation and reduction.

2. A method according to claim 1 where the chlorinated hydrocarbons are selected from the group consisting of perchloroethene, trichloroethene, dichloroethenes, vinyl chloride, tetrachloroethane, 1,1,1-trichloroethane, carbon tetrachloride, chloroform, polychlorinated biphenyls, and mixtures thereof.

3. A method according to claim 1 where the concentrating extraction is a direct extraction for solid material and an indirect extraction with a polar solvent for gaseous media or aqueous solutions.

4. A method according to claim 3 where the indirect extraction uses a hydrophobic substrate interfacing between the gaseous media or aqueous solution.

5. A method according to claim 3 where the solvent is selected from the group consisting of dimethylformamide, acetonitrile, propylene carbonate, dimethyl sulfoxide, and mixtures thereof.

6. A method for detecting and quantifying chlorinated hydrocarbon pollutants in an electrochemical cell comprising:

extracting the chlorinated hydrocarbons from gaseous, aqueous, or solid media into an organic solution; applying controlled reduction potentials to a working electrode in the electrochemical cell to dechlorinate chlorinated hydrocarbon pollutants at the working electrode in the organic solvent; and measuring a reducing peak current or charge generated to determine the chlorinated hydrocarbon pollutant concentration and a reduction potential or potential pattern to identify chlorinated hydrocarbon pollutant species.

7. A method according to claim 6 where the chlorinated hydrocarbons are selected from the group consisting of perchloroethene, trichloroethene, dichloroethenes, vinyl chloride, tetrachloroethanes, 1,1,1-trichloroethane, carbon tetrachloride, chloroform, polychlorinated biphenyls, and mixtures thereof.

8. A method according to claim 6 where the concentrating extraction is a direct extraction for solid material and an indirect extraction with a polar solvent for gaseous media or aqueous solutions.

9. A method according to claim 8 where the indirect extraction uses a hydrophobic substrate interfacing between the gaseous media or aqueous solution.

10. A method according to claim 8 where the solvent is selected from the group consisting of dimethylformamide, acetonitrile, propylene carbonate, dimethyl sulfoxide, and mixtures thereof.

11. A method to destruct chlorinated hydrocarbon pollutants or unsaturated hydrocarbons found in aqueous solutions comprising:

concentrating the chlorinated hydrocarbon pollutants or unsaturated hydrocarbons in a polar solvent by indirect extraction using a hydrophobic substrate interface between the aqueous solution and the polar solvent, where said hydrophobic interface adsorbs the chlorinated hydrocarbon pollutants or unsaturated hydrocarbons and then diffuses said chlorinated hydrocarbon pollutants or unsaturated hydrocarbons into the polar solvent;

passing current at a controlled potential in an electrochemical cell containing three electrodes, said electrodes consisting of a working electrode, a reference electrode, and an auxiliary electrode, through the solvent extractant containing the chlorinated hydrocarbon pollutants or unsaturated hydrocarbons for a period of time to electrochemically remove chlorine from the chlorinated hydrocarbon pollutants or hydrogenate the unsaturated hydrocarbons at a working electrode, where said working electrode is in-situ reactivated for reuse through electrochemical oxidation and reduction.

12. A method to destruct chlorinated hydrocarbon pollutants or unsaturated hydrocarbons found in gaseous media comprising:

collecting the chlorinated hydrocarbon pollutants or unsaturated hydrocarbons in a hydrophobic substrate, said hydrophobic substrate acting as a interface between the gaseous media and a polar solvent;

diffusing the chlorinated hydrocarbon pollutants or unsaturated hydrocarbons from the hydrophobic interface into the polar solvent;

electrochemically removing chlorine from the chlorinated hydrocarbon pollutants or hydrogenating the unsaturated hydrocarbons in an electrochemical cell by passing current at a controlled potential through the solvent containing the chlorinated hydrocarbon pollutants or unsaturated hydrocarbons for a period of time to electrochemically reduce the chlorinated hydrocarbon pollutants or unsaturated hydrocarbons at a working electrode in the electrochemical cell; and reactivating in-situ the working electrode through electrochemical oxidation and reduction.

* * * * *